United States Patent [19]

Kennamer et al.

[11] Patent Number: 5,028,542
[45] Date of Patent: Jul. 2, 1991

[54] GLUCOSE MEASUREMENT CONTROL REAGENT AND METHOD OF MAKING THE SAME

[75] Inventors: Jim Kennamer, Indianapolis; Diane Storhoff, Muncie; Roger Bontrager, Indianapolis; David Tabb, Greenfield; Arthur Usmani, Indianapolis, all of Ind.

[73] Assignee: Boehringer Mannheim Corporation, Indianapolis, Ind.

[21] Appl. No.: 476,085

[22] Filed: Feb. 7, 1990

[51] Int. Cl.$^5$ .................... G01N 31/00; G01N 33/66
[52] U.S. Cl. .................... 436/14; 252/408.1; 435/14; 436/8; 436/95; 436/18
[58] Field of Search .................... 436/8–18, 436/95; 252/408.1; 435/14

[56] References Cited

U.S. PATENT DOCUMENTS

| | | | |
|---|---|---|---|
| 3,682,835 | 8/1972 | Louderback | 436/14 |
| 3,920,580 | 11/1975 | Mast | 436/14 |
| 4,517,301 | 5/1985 | Greene | 436/14 |
| 4,684,615 | 8/1987 | Hoskins | 436/14 |
| 4,729,959 | 3/1988 | Ryan | 436/14 |
| 4,731,330 | 3/1988 | Hill et al. | 436/16 |

*Primary Examiner*—Robert J. Hill, Jr.
*Attorney, Agent, or Firm*—Felfe & Lynch

[57] ABSTRACT

The invention relates to a non-serum based control reagent for glucose determination. Rather than using modified serum, the control reagent contains water, glucose, and the viscosity agent polystyrene sulphonate. The control reagent may also contain a buffer, preservatives, surfactants or surface active agents. A method of making the control reagent is also disclosed.

19 Claims, No Drawings

[5,028,542]

GLUCOSE MEASUREMENT CONTROL REAGENT AND METHOD OF MAKING THE SAME

FIELD OF THE INVENTION

This invention relates to control reagents useful in validating testing devices, such as test strips and dipsticks. More particularly, it relates to a non-serum based, aqueous glucose control reagent.

BACKGROUND AND PRIOR ART

The field of clinical chemistry and clinical analysis is concerned, inter alia, with the determination and quantification of various substances in body fluids. Many examples of the substance which are to be determined can be given, and include cholesterol, urea, cations, and glucose. These examples of analyte, as well as others, are assayed in diverse body fluids such as urine and blood.

One of the most frequently used devices in clinical chemistry is the test strip or dipstick. These devices are characterized by their simplicity of use. Essentially, the device is contacted to the body fluid to be tested. Various reagents incorporated into the device react with the analyte being determined to provide a detectable signal. Generally, this is a color or a change in color. These signals are measured or determined either visually or, more preferably, by an analysis machine. The detectable signal is correlated to a standard, so as to give a value for the amount of analyte present in the sample.

It will be understood that clinical analysis of the type described herein requires that any testing system be extremely accurate. In particular, when automated systems are used, it is essential to ensure that the elements of the analysis be reliable, and that the measurement taken be valid. It is for this purpose that control reagents are used.

Tietz, et al., *Textbook of Clinical Chemistry* page 430, defines "control material" as "a specimen, or solution, which is analyzed solely for quality control purposes and is not used for calibration purposes". This standard reference work goes on to describe some of the requisites of a control material, as follows: "They need to be stable materials, available in aliquots or vials, that can be analyzed periodically over a long time. There should be little vial-to-vial variation so that differences between repeated measurements can be attributed to the analytical method alone". It must be added that the control material must be stable as well.

The cited reference, at page 433, discusses how the matrix of the control material should be the same as the material being analyzed. To that end, Tietz discusses modified human serum as one type of control material. Indeed, the art now recognizes the term "control serum" as referring to control material based upon serum. This terminology will be used herein, and is different from the term "control reagent" which, as used hereafter, refers to a control material which is not based on, and does not contain, serum of any type.

As has been pointed out, supra, one of the criteria which control materials have to satisfy is stability. Control materials based upon serum, however, are inherently unstable, due to the various components contained therein. Further, sera will vary from source to source, so uniformity from lot to lot cannot be guaranteed. Thus, it is sometimes desirable to have a control material based on a non-serum or serum free medium.

Examples of serum free control media, or "control reagents" as used herein, are seen in U.S. Pat. Nos. 4,684,615 and 4,729,959. The '615 patent teaches an aqueous isoenzyme control reagent. The reagent contains the isoenzyme of interest, together with other materials in a water base. More pertinent to the subject invention is the '959 patent, which is directed to "a stable glucose reference control". This control contains glucose in a range of from about 40 to 500 mg/dl, together with fixed red blood cells, in an aqueous solution. The range of glucose concentrations given are sufficient to cover just about all ranges of glucose found in, e.g., blood.

The '959 patent points to a problem with aqueous control reagents at column 1, lines 50–55. Briefly, erythrocytes impart a degree of viscosity to blood which is absent in water based systems. This problem was also recognized in U.S. Pat. No. 3,920,580 to Mast. This patent teaches that aqueous solutions had not been consistent, and that a lack of reproduceability was observed when dry reagent strips were used with such materials. Mast taught that suitable reagents could be prepared using an antidiffusing agent in combination with glucose and water. The antidiffusing agents include polyvinylpyrrolidone, polyvinyl alcohol, polyethylene glycol, dextran, and bovine serum albumin.

It has now been found that a suitable glucose control reagent can be formed without using any of the material referred to in Mast as required ingredients. Rather, by combining a soluble polymer with glucose and water, with additional optional materials, a suitable glucose control reagent can be made.

SUMMARY OF THE INVENTION

The invention is a non-serum based glucose control reagent which comprises a predetermined known amount of glucose, water, and a soluble polymer, i.e., a polystyrene sulphonate or a soluble salt thereof. Additional materials, such as a buffer, a preservative, a surface active agent or a surfactant, or an ionic salt, either alone or in various additive combinations, may be mixed with the three required components. Another aspect of the invention is a method of making the control reagent by mixing the glucose and the polystyrene sulphonate together.

DETAILED DESCRIPTION OF PREFERRED EMBODIMENTS

Example 1

A preferred formulation of the control reagent of the invention was prepared, as follows:

| | |
|---|---|
| $H_2O$ | 738.6 g |
| Na Salt of polystyrene sulfonate | 250.0 g |
| HEPES (4-(2-hydroxyethyl-1-piperazine-ethane sulfonic acid) | 7.1 g |
| 2-phenoxyethanol | 3.31 g |
| Germall 115 | 3.0 g |
| Methylparaben | 1.20 g |
| TOTAL weight: | 1003.21 g |

This reagent was adjusted with 10N NaOH to have a final pH of 7.5.

The formulation described here then has glucose added to the rest of the reagent in a predetermined amount. The skilled artisan will recognize that the concentration will vary, at the discretion of the maker and depending upon the particular test system involved. Ryan, U.S. Pat. No. 4,729,959, e.g., sets forth a range of from 40 to 500 mg/dl, of glucose. This range covers most of the concentrations of clinical interest, but it is assumed herein that the amount of glucose in the claimed control reagent may be both less than or more than the range recited in the Ryan patent.

Example 2

The control reagent set forth in Example 1 was then tested for its efficacy. As explained supra, one of the most important features of a control reagent is its consistency, meaning that values obtained using it should be fairly uniform from run to run.

With this in mind, the control reagent of Example 1 was applied to test strips containing the glucose determination system described in U.S. patent application Ser. No. 339,051, filed Apr. 14, 1989, now U.S. Pat. No. 4,929,545, the disclosure of which is incorporated by reference. Briefly, this reference describes determining glucose using a reagent containing a glucose oxidase, ferricyanide/ferric compound system.

Three glucose solutions were prepared, containing 41 mg/dl, 120 mg/dl, and 174 mg/dl glucose, as measured via glucose hexokinase methodology. These solutions were then measured using the exemplified reagent, together with the reference glucose determination reagent. The results are set forth in Table 1:

TABLE I

| Strip Response Values at Three Glucose Levels | | | |
|---|---|---|---|
| Strip Glucose Values (mg/dl) | 56 | 183 | 227 |
| | 56 | 182 | 239 |
| | 63 | 187 | 248 |
| | 50 | 181 | 238 |
| | 63 | 191 | 243 |
| | 58 | 185 | 249 |
| | 53 | 179 | 224 |
| | 63 | 191 | 234 |
| | 63 | 190 | 235 |
| | 57 | 174 | 221 |
| | 56 | 175 | 238 |
| | 61 | 182 | 240 |
| | 51 | 173 | 238 |
| | 62 | 186 | 235 |
| | 60 | 178 | 245 |
| | 53 | 172 | 229 |
| | 65 | 180 | 250 |
| | 65 | 184 | 250 |
| | | 186 | 252 |
| Mean Strip Glucose Value (mg/dl) | 58.7 | 182.0 | 238.5 |
| Standard deviation | 4.8 | 5.9 | 9.1 |
| CV % | 8.2 | 3.2 | 3.8 |
| Hexokinase Glucose Value (mg/dl) | 41 | 120 | 174 |

These results show a level of consistency well within that required of a control reagent, as is indicated by the standard deviation and coefficient of variation values reported for each set of tests.

While the control reagent system has been shown to be operative with respect to the glucose oxidase/ferrocyanide/ferricyanide system, it will be understood that the criteria which the control reagent must satisfy are independent of the actual test system. Thus, the control reagent will be seen to be useful in connection with any of the known glucose analysis systems.

Essential to the invention are a predetermined amount glucose, water, and the recited polystyrene sulphonate. The water is used, of course, to create a reagent solution. By "predetermined" is meant that, prior to formulation of the actual reagent, a concentration of glucose has been selected. This concentration may vary, as those skilled in the art will recognize. As has been mentioned supra, the art recognizes, e.g., a range of from 40 to 500 mg/dl, but one may envision lower ranges to, e.g., about 20 mg/dl. Some typical ranges would be from about 60 to about 240 mg/dl, or from about 60 to about 300 mg/dl.

The essential features of the invention, when the reagent is in the form of a solution, are the solvent (water), the predetermined amount of glucose, and the polystyrene sulphonate or a salt thereof. The polystyrene sulphonate or its salt may be present, in e.g., from about 0.5 to about 55–60 weight percent of the reagent. A preferred range is from about 0.5 to about 40 weight percent of the control reagent. In an especially preferred embodiment a range of from about 20 to 30 weight percent is used. The weight percent of the polymer will vary, depending upon factors which include molecular weight and solubility.

The term "polystyrene sulphonate" refers to any and all forms of this molecule. As is known, polymers can vary in their atomic weight. In the case of polystyrene sulphonate, an atomic weight of from about 5000 to about 6,000,000 is preferred. An especially preferred embodiment uses polystyrene sulphonate at an atomic weight of from about 35,000 to about 750,000. Most preferably, the atomic weight ranges from about 70,000 to about 500,000.

Optional additional components of the control reagent include buffers, preservatives, surface active agents, surfactants, and ionic salts. With respect to buffers, some preferred species are HEPES (4-(2-hydroxy ethyl-1-piperazine-ethane sulphonic acid); CHES(2-(N-cyclohexylamino) ethane sulphonic acid); MOPS(3-(N-morpholino)propane sulphonic acid), and MEPS(2-(N-morpholino) ethane sulphonic acid) and CAPS (3-(cyclohexylamino)-1-1-propane)-sulfonic acid) buffers. Preferred preservatives include imidazolidinyl urea, available under the trade name "Germall 115," methylparaben or methanol (((2-(dihydro-5-methyl-3(2H)-oxazoylyl)-1-methylethoxy)methoxy)methoxy), available as "Cosan 145", phenoxyethanol and gentamycin sulfate, both individually and in combination. Typical surfactants include "MIRANOL J2M-SF", which is capryloamphocarboxypropionate, and "DOWFAX 2Al", which is tetrapropylene diphenyloxide disulphonate sodium salt.

The reagent may also contain an ionic salt, such as an ionic salt of sodium (e.g., sodium sulphate) or salts of other cations such as lithium, magnesium, calcium, and so forth.

It may also be desirable to include a colored or colorable substance in the reagent. This can be desirable because body fluid samples frequently possess a color as one of their properties. As the control reagent is being used to calibrate per a body fluid sample, it can be useful to calibrate against conditions as similar to the tested fluid as possible, including color.

The control reagent may also be formulated as either a kit, or in the form of a lyophilisate. "Lyophilisate" as the art recognizes, refers to the substantial absence of moisture in a formulation. The invention, in lyophilized form, most broadly comprises a predetermined amount of glucose and the polystyrene sulphonate or salt thereof. Additional components, including those listed supra, may be included in the lyophilisate, as long as moisture is substantially absent.

When the reagent is present in kit form, it can include, e.g., a sample of a solution of a predetermined amount of glucose in one container means, and polystyrene sulphonate in a second one with a container means holding both the first and second containers. Additional components may also be present, as listed supra, and may be mixed with either of the first two components, or may be present in separate container means.

It will be understood that the specification and examples are illustrative but not limitative of the present invention and that other embodiments within the spirit and scope of the invention will suggest themselves to those skilled in the art.

We claim:

1. Serum-free control reagent for glucose determination comprising a mixture of:
   (i) a predetermined amount of glucose,
   (ii) water, and
   (iii) polystyrene sulphonate or a salt thereof.

2. Serum-free control reagent of claim 1, wherein said polystyrene sulphonate is present in an amount ranging from about 0.5 to about 60 weight percent of said control reagent.

3. Serum-free control reagent of claim 2, wherein said polystyrene sulphonate is present in an amount ranging from about 20 to about 30 weight percent of said control reagent.

4. Serum-free control reagent of claim 1, wherein said polystyrene sulphonate is present in an amount ranging from about 0.5 to about 40 weight percent of said control reagent.

5. Serum-free control reagent of claim 1, wherein said polystyrene sulphonate has an atomic weight of from about 5000 to about 6,000,000.

6. Serum-free control reagent of claim 5, wherein said polystyrene sulphonate has an atomic weight of from about 35,000 to about 750,000.

7. Serum-free control reagent of claim 6, wherein said polystyrene sulphonate has an atomic weight of from about 70,000 to about 500,000.

8. Serum-free control reagent of claim 1, further comprising a buffer.

9. Serum-free control reagent of claim 8, wherein said buffer is selected from the group consisting of 4-(2-hydroxy ethyl-1-piperazene-ethane sulphonic acid),
   2-(N-cyclohexylamino)ethane sulphonic acid,
   3-(N-morpholino)propane sulphonic acid,
   2-(N-morpholino)ethane sulphonic acid, and
   3-(cyclohexylamino)-1-1-propane-sulphonic acid.

10. Serum-free control reagent of claim 1, further comprising at least one preservative.

11. Serum-free control reagent of claim 10 wherein said preservative is imidazolidinyl urea, methylparaben, methanol(((2-(dihydro-5-methyl-3(2H)-oxazolyl)-1-methylethyloxy)methoxy) methoxy), phenoxyethanol, or gentamyacin sulphate.

12. Serum-free control reagent of claim 1, further comprising a surfactant.

13. Serum-free control reagent of claim 1, further comprising an ionic salt.

14. Serum-free control reagent of claim 1, further comprising a colored or color forming compound.

15. Serum-free control reagent for glucose determination consisting essentially of a mixture of:
    (i) glucose,
    (ii) water,
    (iii) polystyrene sulphonate or a salt thereof,
    (iv) a preservative, and
    (v) a surfactant or surface active agent.

16. Lyophilized, serum-free control reagent comprising a mixture of a predetermined amount of glucose, and a polystyrene sulphonate or salt thereof.

17. Process for making a serum free glucose control reagent comprising mixing a predetermined amount of glucose with a polystyrene sulphonate or salt thereof.

18. Process of claim 17, further comprising mixing water with said glucose and polystyrene sulphonate.

19. Process of claim 17, further comprising mixing at least one material selected from the group consisting of a buffer, a preservative, a surfactant, an inorganic salt and a colored or color forming compound to said predetermined amount of glucose and polystyrene sulphonate or salt thereof.

* * * * *